US012193893B2

(12) United States Patent
Kettu et al.

(10) Patent No.: US 12,193,893 B2
(45) Date of Patent: Jan. 14, 2025

(54) OPERATING LIGHT FOR DENTAL CARE

(71) Applicant: PLANMECA OY, Helsinki (FI)

(72) Inventors: Antti Kettu, Helsinki (FI); Ari Forsberg, Helsinki (FI)

(73) Assignee: PLANMECA OY, Helsinki (FI)

( * ) Notice: Subject to any disclaimer, the term of this patent is extended or adjusted under 35 U.S.C. 154(b) by 328 days.

(21) Appl. No.: 17/437,687

(22) PCT Filed: Mar. 12, 2020

(86) PCT No.: PCT/FI2020/050158
§ 371 (c)(1),
(2) Date: Sep. 9, 2021

(87) PCT Pub. No.: WO2020/183067
PCT Pub. Date: Sep. 17, 2020

(65) Prior Publication Data
US 2022/0160461 A1 May 26, 2022

(30) Foreign Application Priority Data
Mar. 12, 2019 (FI) ........................... 20190017

(51) Int. Cl.
| H04N 7/18 | (2006.01) |
|---|---|
| A61B 90/30 | (2016.01) |
| A61B 90/35 | (2016.01) |
| A61C 1/00 | (2006.01) |
| A61C 1/08 | (2006.01) |
| A61B 17/00 | (2006.01) |
| A61B 34/20 | (2016.01) |
| A61B 90/00 | (2016.01) |
| G06F 3/01 | (2006.01) |

(52) U.S. Cl.
CPC .............. *A61C 1/088* (2013.01); *A61B 90/30* (2016.02); *A61B 90/35* (2016.02); *A61C 1/0007* (2013.01); *A61C 1/082* (2013.01); *A61B 2017/00207* (2013.01); *A61B 2034/2065* (2016.02); *A61B 2090/366* (2016.02); *G06F 3/017* (2013.01)

(58) Field of Classification Search
CPC ....... A61C 1/088; A61C 1/0007; A61C 1/082; G61B 90/30; G61B 90/35; G61B 2034/2065; G61B 2090/366; G61B 2017/00207; G06F 3/017; H04N 7/18
USPC ........................................................... 348/64
See application file for complete search history.

(56) References Cited

U.S. PATENT DOCUMENTS

| 2005/0128184 A1 | 6/2005 | McGreevy |
| 2005/0195587 A1 | 9/2005 | Moctezuma De La Barrera et al. |
| 2011/0135190 A1 | 6/2011 | Maad |

(Continued)

OTHER PUBLICATIONS

International Search Report for PCT/FI2020/050158, Mailed Jun. 15, 2020, 3 pages.

*Primary Examiner* — Trang U Tran
(74) *Attorney, Agent, or Firm* — Lippes Mathias LLP

(57) ABSTRACT

The invention relates to a projector construction (86) arranged both structurally and operatively integrated into a dental operating light (8) so as to be a part of the dental operating light (8) and wherein the dental operating light (8) illuminates a first area on a surface whereas the projector construction (86) is configured to project graphics, pictures and/or video in essentially the same direction as the operating light (8) on the surface, on a second area.

19 Claims, 7 Drawing Sheets

(56) References Cited

U.S. PATENT DOCUMENTS

| | | |
|---|---|---|
| 2015/0177598 A1 | 6/2015 | Mima et al. |
| 2016/0180046 A1 | 6/2016 | Sezeur et al. |
| 2017/0367785 A1* | 12/2017 | Munari .................. H05B 47/19 |
| 2019/0324253 A1* | 10/2019 | Zapata .................. G02B 21/084 |
| 2020/0030054 A1* | 1/2020 | Okawara ................ A61C 19/04 |
| 2023/0031165 A1* | 2/2023 | Rubbert ............... A61C 9/0046 |

\* cited by examiner

OPERATING LIGHT FOR DENTAL CARE

FIELD OF INVENTION

The invention relates to arrangements implementable in connection with dental operating lights.

BACKGROUND OF INVENTION

In the field of odontology, the term dental care unit (often simply just 'dental unit') refers to an apparatus or an arrangement which supplies power and also possibly control signals to diagnostic instruments related to dental care or to instruments used in connection with dental care operations. One typical solution is to arrange such instruments on an instrument console which is supported by a support arm extending from frame structures of the dental care unit.

In a dental care unit has also often been arranged an arm for an operating light. For such operating lights, there are standards related to illuminating particularly a patient's mouth area, which standards define properties of the light field generated by the operating light such as its size, shape, penumbral area etc. Dental operating lights are also known as stand-alone products, or sold as independent articles yet arranged to be connectable to a dental care unit.

State of the art dental care units typically include an arrangement to present various information relating to dental care work. This information may include, for example, basic settings of an instrument connected to the dental care unit, more detailed information relating to operation of the instrument during use of the instrument, and on the other hand other kind of information relating to e.g. guiding dental care work. This kind of information is known to be displayed e.g. on a dental care unit's user interface or on a monitor connected to the dental care unit. One location for displaying such information is a support structure for dental instrument(s).

BRIEF DESCRIPTION OF INVENTION

The object of the invention is to provide technology which enables bringing information relating dental care work close to a dentist's field of view when operating in an oral cavity.

For one, as one aspect of the invention, as an example, the information may relate to the very operation being currently under way or to the use of the instrument currently having been picked up for use from the support structure for the instrument.

According to one aspect of the invention, as an example, a light beam projecting graphics, pictures and/or video may be generated in a dental operating light basically in the same direction as in which the operating light is arranged to generate the desired kind light pattern, in a desired direction and at a desired distance from the operating light to illuminate a patient's oral cavity.

According to one aspect of the invention, as an example, a projector construction arranged to a dental operating light may be configured to enable projecting graphics, pictures and/or video at an area larger than an area covered by said desired light pattern at a desired distance from the operating light.

According to one aspect of the invention, as an example, the projector arranged to the operating light comprises a control system which may be configured to project as a default, or as a response to a control signal, graphics, pictures and/or video within the area larger than the area covered by the desired light pattern at an area outside the area covered by the desired light pattern.

According to one aspect of the invention, as an example, the area on which graphics, pictures and/or video is arranged to be projected, within the area larger than the area covered by the desired light pattern, is an area above or below the desired light pattern illuminating patient's oral cavity, such as a patient's forehead or a part of patient's torso.

According to one aspect of the invention, as an example, the area on which graphics, pictures and/or video is projected may be patient's eye protectors or a reflecting structure arranged connected to the patient's eye protectors.

According to one aspect of the invention, as an example, a flash at certain intervals (or count down/up remaining time) is generated and projected to inform about elapsed time during a given dental operation.

According to one aspect of the invention, as an example, a color coded graphics can be generated and projected, relating e.g. to instrument's position during a procedure when an instrument navigation is activated.

According to one aspect of the invention, as an example, information about, an actual position or a deviation of an instrument from a target position may be projected during instrument navigation.

According to one aspect of the invention, as an example, subtle information about a reserved time for a patient nearing its end may be projected.

According to one aspect of the invention, as an example, essential information related to instruments or to functions of the dental care unit may be projected, thus augmenting or replacing a traditional user interface of a dental care unit.

According to one aspect of the invention, as an example, a gesture recognition feature may be included with projecting a user interface, while gestures may be observed e.g. by a camera arrangement additionally included in the operating light. A gesture may be arranged to be recognized as a control signal relating to a feature of a dental care unit or a dental instrument being projected, such as a feature of user interface or a part of a user interface begin projected.

According to one aspect of the invention, as an example, the dental care unit is arranged to be a part of a system comprising a means for a pattern recognition. Patterns configured to be recognized may include, as an example, a mouth, eyes, eye protectors.

According to one aspect of the invention, for example, a novel kind of operating light at least functionally connectable to a dental care unit is designed comprising a projector arrangement, wherein the projector arrangement has already originally been designed as an integral part of the structure of the operating light.

According to one aspect of the invention, for example, a novel, kind of operating light functionally connectable to a dental care unit is designed which further comprises a camera arrangement, wherein the camera arrangement has already originally been designed as an integral part of the structure of the operating light. According to one aspect of the invention, for example, the camera arrangement comprises a stereo camera, that is, two cameras located at a distance from each other. Such an arrangement can be utilized in connection with e.g. drilling a hole required for a dental implant, to generate information on the position and location of the drill with respect to the hole designed for the implant.

The essential characteristics of the invention will be defined in the accompanying independent claims.

Some preferred embodiments of the invention will be presented in the accompanying dependent claims and in the following more detailed description of the invention.

DETAILED DESCRIPTION OF INVENTION

Figure 1:
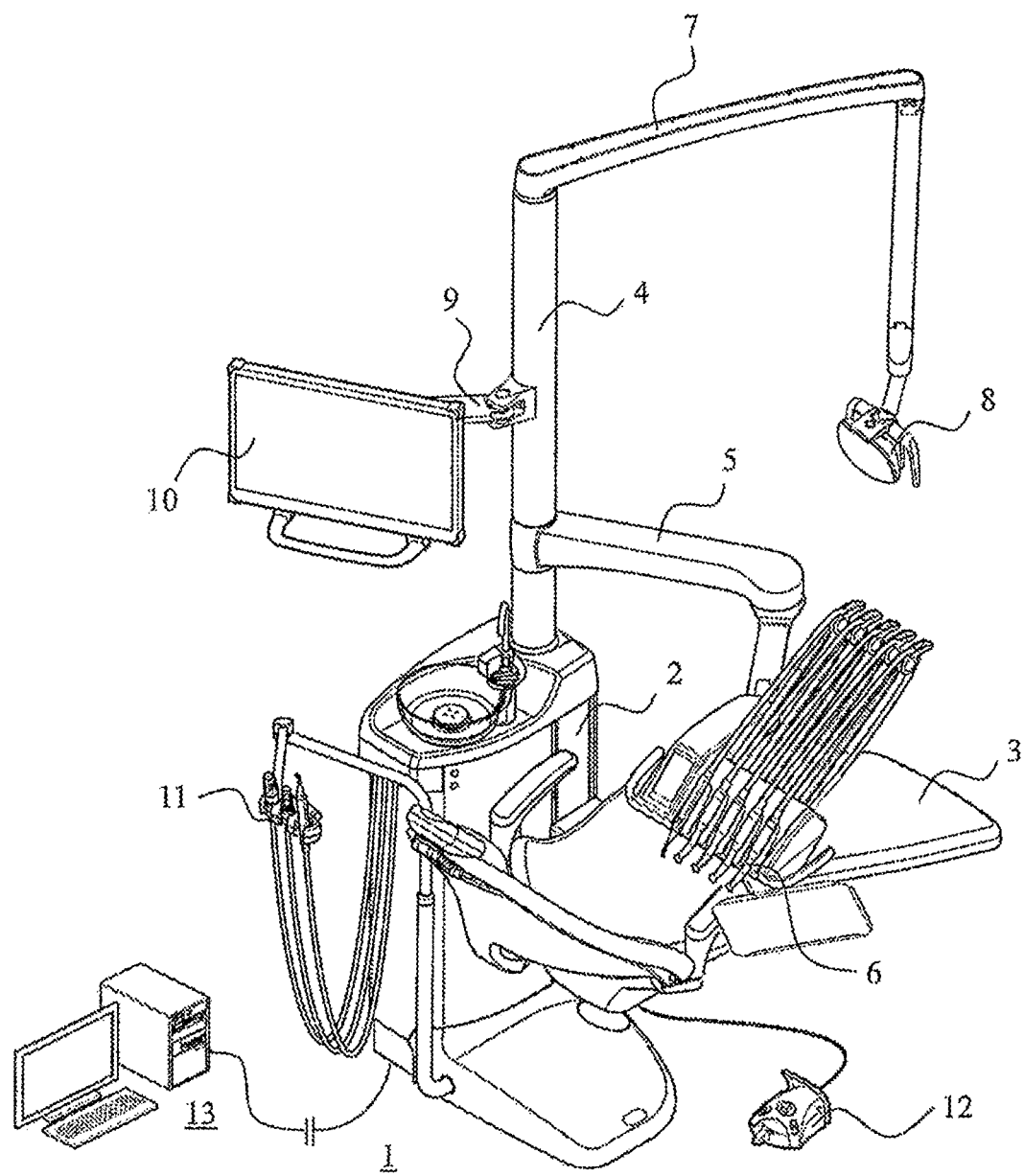
FIG. 1 shows an example of a typical dental care unit.

FIG. 1 shows a basic structure of one typical dental care unit 1 designed for use in connection with dental care and, thus, being an example of a dental care unit applicable for use to implement the invention. However, FIG. 1 shows merely an example of such dental care units and there are components which are not necessary to be included in a dental care unit according to the invention.

The dental care unit 1 according to FIG. 1 comprises a frame structure 2 and a patient chair 3 connected to it. From the frame structure 2 extends a vertical structure 4 to which connects a first support construction 5 for supporting dental instruments 6, which may be e.g. diagnostic instruments related to dental care and/or instruments used in connection with dental care operations. Also to said vertical, structure 4 connects a second support structure 7 for an operating light 8 and a third support structure 9 for a display 10.

FIG. 1 also shows an instrument console 11 which may be designed to support instruments typically used by a dental assistant, and a foot control 12 by which the operations of the dental care unit 1 and/or apparatuses and structures related to or connected to it can be controlled. Not shown in FIG. 1, a dental care unit 1 can also comprise another kind of user interface, such as a touch screen, as a part of its control system. Additionally, the dental care unit 1 of FIG. 1 is arranged into operational connection with a data network or an individual computer 13.

As said, it should be noticed that the dental care unit according to FIG. 1 is only an example. Within the scope of the invention, the dental care unit can comprise more or less support structures for different kinds of components and apparatus than shown in the structure according to FIG. 1. There is also no need to have a patient chair, for instance, in the dental care unit; itself as it may be implemented as a structure separate from the frame of the dental care unit. Furthermore, the frame structure of the dental care unit may be, instead of how the structure is shown in FIG. 1 as having significant horizontal and vertical dimensions, only a support structure basic of its dimensions and from which extends one or more support arms. The frame may also be arranged integrated to the structures of a floor-attached patient chair.

However, the frame structure of the dental care unit has been typically implemented such that via it has been arranged to be supplied power and/or control signals required for the use of instruments and apparatuses utilized in connection with dental care. Physically, that means supplying e.g. at least one of the following: water, compressed air, electricity, an electric or other control signal. Hence, when a dental care unit is mentioned in this application, it refers to a structure which includes an arrangement for supplying at least some of the above-listed or equivalents to dental-care instruments arranged into connection with the dental care unit or other apparatuses utilized in connection with dental care.

Figure 2:
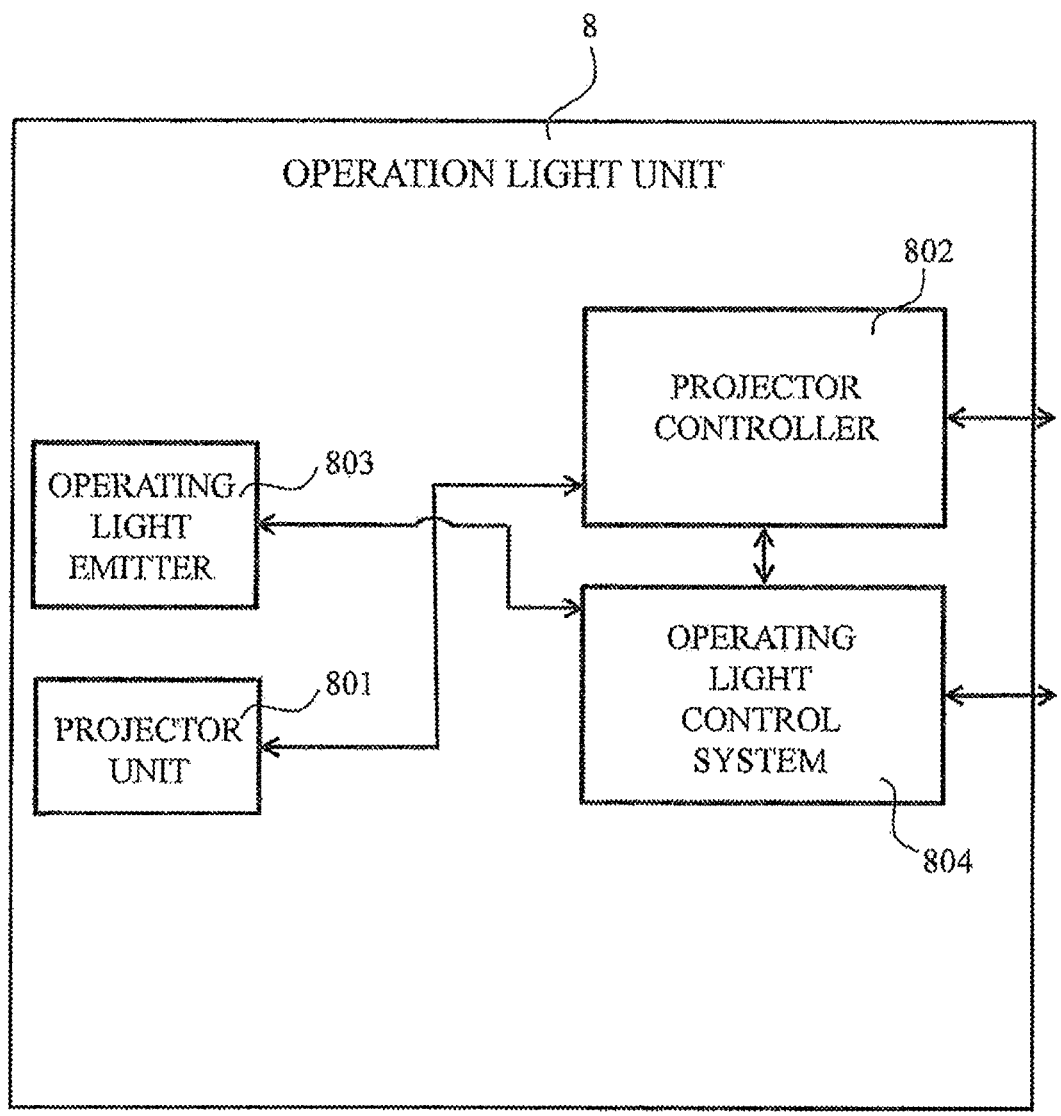
FIG. 2 shows a block diagram of one possible arrangement, to implement an integration of a projector to a dental operating light.

FIG. 2 shows a block diagram of one possible arrangement to implement the integration of a projector to a dental operating light. The arrangement in accordance with FIG. 2 comprises a projector unit 801 which is arranged into operational connection with a projector controller 802. As also shown, the projector controller 802 may be arranged in operational connection with a control system 804 of the operating light 8. The control system 804 of the operating light 8 controls a light-emitter 803 of the operating light and may also be arranged to communicate with it.

Figure 3:
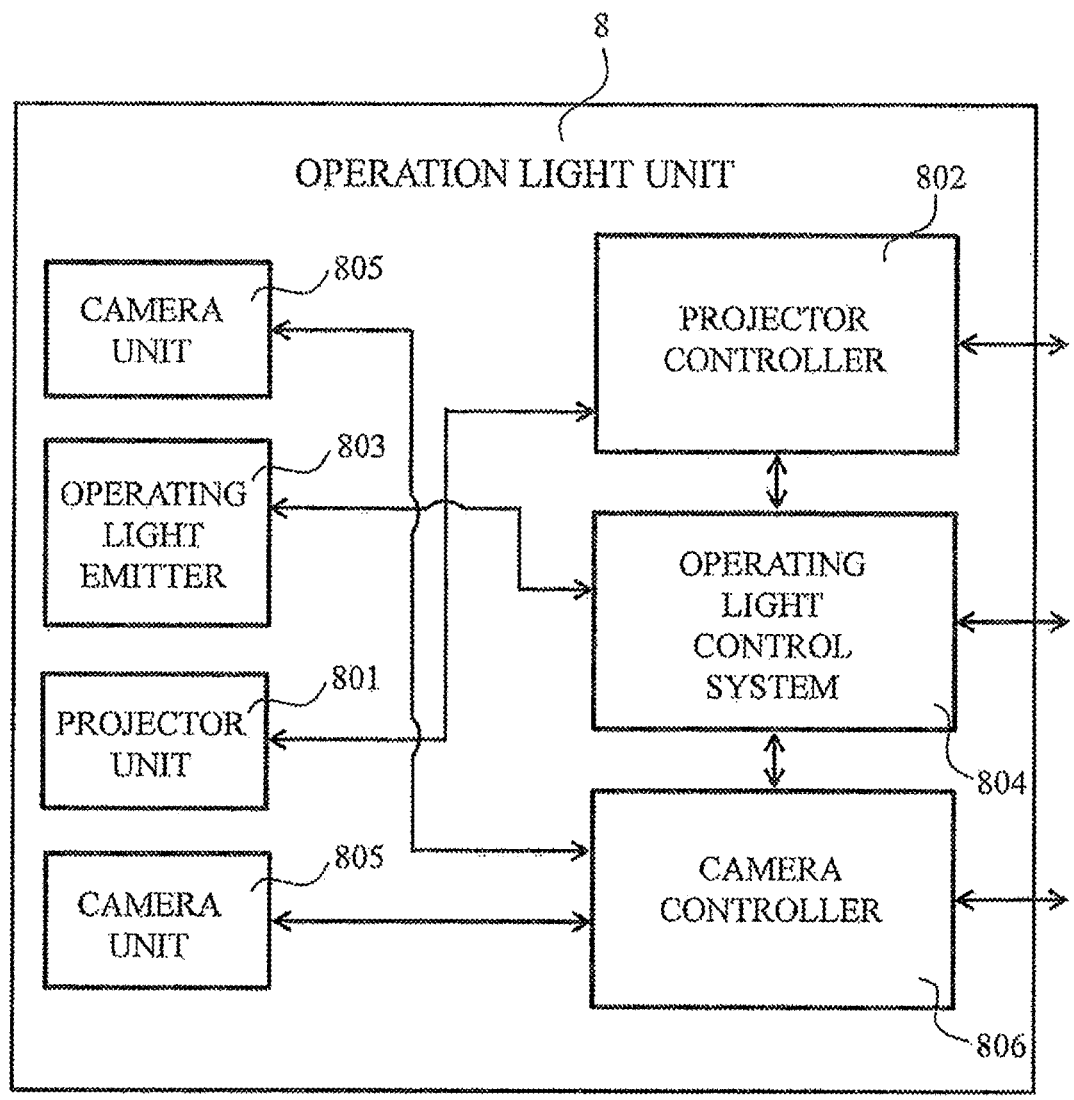
FIG. 3 shows a block diagram of one possible arrangement to implement an integration of a projector and a stereo camera to a dental operating light.

In the embodiment of the invention according to FIG. 3, the operating light 8 further includes a stereo camera, i.e. two camera units 805 and a camera controller 806. In the embodiment of the invention according to FIG. 4, resources (like controller 802) of the projector unit 801 and of the stereo camera 805 are integrated into a single controller 802 while according to one aspect of the invention, the resources are just partially integrated.

Figure 5:
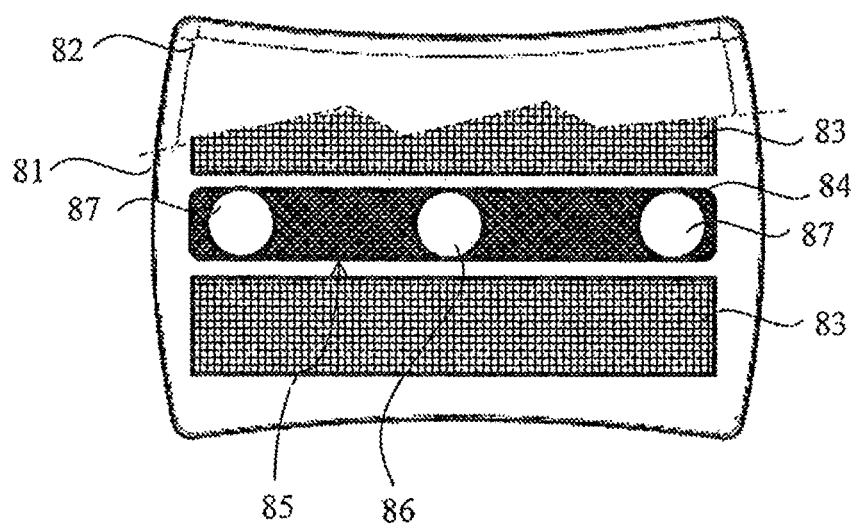
FIG. 5 shows a (partially) schematic example of one arrangement according to the invention of a part of a dental operating light.

FIG. 5 shows, as a schematic example, one arrangement according to the invention for a dental operating light of a dental care unit (without showing the support arm structure). The operating light 8 of FIG. 2 comprises a frame part 81 and a cover glass 82, shown only partially in FIG. 2 to enable a view at some internal components of the operating light 8. In the example of FIG. 2, the structures designed to generate a desired kind light pattern in a desired direction and at a desired distance from the operating light include reflecting structures 83 designed to reflect light produced by light emitting means 85, not visible in FIG. 2 while begin located underneath a support structure 84. The projector 86 is arranged on the support 84, in FIG. 5 in the middle of the operating light 8. FIG. 5 also shows two optical cameras 87 arranged close to the sides of the operating light 8.

Figure 6:
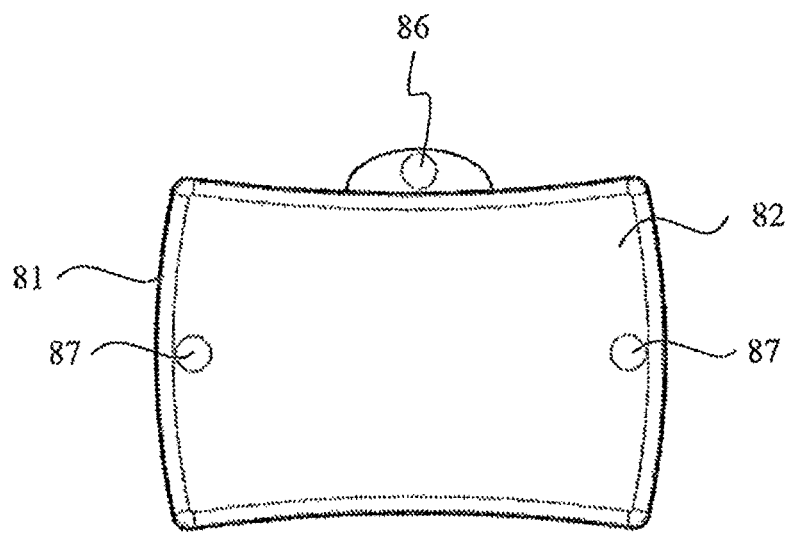
FIG. 6 shows another example of an arrangement according to the invention of a part, of a dental operating light.

In FIG. 6, a few of the same basic components of the operating light 8 are presented as in FIG. 5 yet there, the location of the projector 86 is arranged to be different. Still, also in this embodiment, the controlling and other functions of the projector 86 may be arranged the same way as discussed above e.g. in the context of discussing FIGS. 2-4, and further in the below.

Figure 7A:
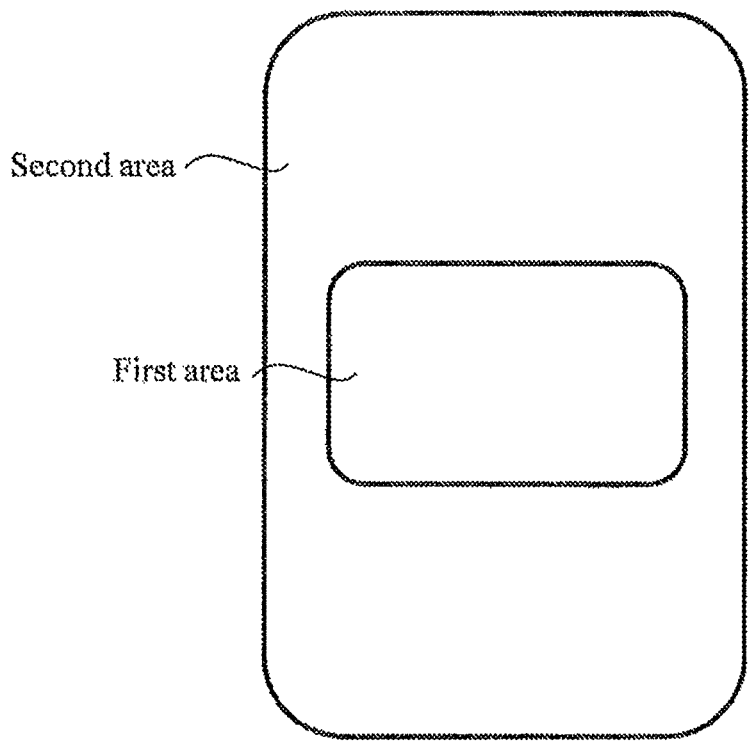
FIGS. 7a and 7b show examples of how a second area, whereto graphics, pictures and/or video may be projected by a projector of the operating light, may be configured to be located in relation to a first area, which is the area on which a desired kind light pattern in a desired direction and at a desired distance from the operating light is generated, to illuminate a patient's oral cavity.
Figure 7B:
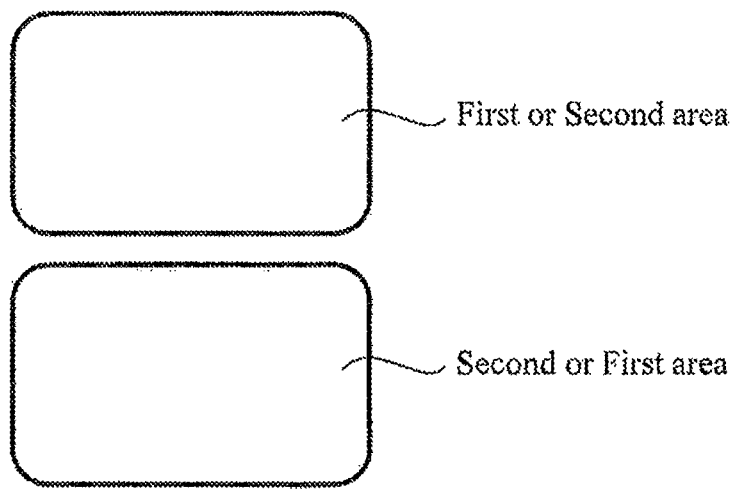

FIGS. 7a and 7b show examples of how a second area, whereto graphics, pictures and/or video may be projected by the projector 86 of the operating light, may be configured to be located in relation to a first area, which is the one on which a desired kind light pattern in a desired direction and at a desired distance from the operating light is generated to illuminate a patient's oral cavity.

Shown in FIG. 7a is an embodiment wherein the projector projects or projector controller 802 is configured to enable projecting graphics, pictures and/or video such that, at a proximity of the desired distance referred to above, the second area is larger than the first area.

In the embodiment of FIG. 7a, the second area is not only larger than the first area as such but it encompasses the first area.

In the embodiment of FIG. 7b, the projector projects or the projector controller 86 is configured to enable projecting, optionally as a default or as a response to a control signal the graphics, pictures and/or video at the second area wherein, at a proximity of the desired distance, the second area is outside but in close proximity to the first area.

According to another aspect of the invention, the projector projects or the projector controller 802, which may be structurally integrated into the operating light 8, is configured to project graphics, pictures and/or video at a first part within the second area as discussed above and simultaneously not to project anything on a second part within the second area.

According to another aspect of the invention, the operating light comprises other means than the projector controller 802 for not to project anything on the second part within the second area as discussed above.

In general, the invention may thus be characterized as being a dental care unit, comprising:
- a frame structure 2;
- a support construction 5 for supporting at least one dental instrument 6, a diagnostic instrument related to dental care and/or at least one instrument used in connection with a dental care operation;
- a control system;
- a user interface 12;
- an arrangement via which to said at least one instrument 6 can be delivered power, or control signals, or both, needed for their operation;
- an operating light 8 arranged for use in connection with dental care comprising a lighting system 83, 85 arranged to generate a desired kind light pattern in a desired direction and at a desired distance from the operating light 8, to illuminate a first area;
- a support structure 7 of the operating light;

and wherein a projector construction 86 is configured to project graphics, pictures and/or video in essentially the same direction as said desired direction on a surface, the surface comprising a second area whereto the graphics, pictures and/or video is projected, the projector construction 86 being both structurally and operatively integrated into the operating light 8 to be a part of the operating light 8.

According to yet another aspect of the invention, the projector controller 86 is configured to receive information relating to projecting graphics, pictures and/or video to be projected from a dental instrument, which instrument may be one related to dental care or used in connection with a dental care operation, from a control system of either the instrument itself, or from the dental care unit when controlling operation of the dental instrument.

According to yet another aspect of the invention the graphics, pictures and/or video comprises a user interface of the dental care unit or a part thereof.

According to yet another aspect of the invention, the operating light arranged with at least one camera 87 is configured to shoot at least partly the second area discussed above.

According to yet another aspect of the invention, the operating light comprises or is in functional connection with a means configured to recognize a gesture within a field of view of a camera 87 arranged to the operating light.

According to yet another aspect of the invention, the control system of the dental care unit is configured to recognize a gesture shot by said at least one camera as a control signal when said gesture is made when said graphics, pictures and/or video is being projected by said projector and comprises a given feature of a user interface (12) of the dental care unit.

According to yet another aspect of the invention, the dental care unit with an operating light and a projector 86 is a part of a system comprising a stereo camera arranged to the operaring light, a means for pattern recognition and a means to project said graphics, pictures and/or video at an area covered by or comprising a given pattern configured to be recognized by said means for pattern recognition, and/or a means to project said graphics, pictures and/or video at an area outside the area covered by or comprising the given pattern configured to be recognized by said means for pattern recognition.

The pattern to be recognized may be e.g. eyes or eye protectors, or a reflecting surface of a given shape designed to be held on a chest of a patient during a dental care operation.

According to yet another aspect of the invention, a system including the dental care unit may comprise a stereo camera arranged to the operaring light, a means for pattern recognition and a means to project at said second area a drilling plan including location and orientation of a hole to be drilled in an anatomy, together with an image or a part of an image shot by said stereo camera including a given pattern recognized by the means for pattern recognition, wherein said given pattern is a pattern arragned to a dental drill instrument.

According to yet another aspect of the invention, at least part of electronics of both the operating light 8 itself and the projector 86, needed for their operation, is arranged as a physical part of a structure of the operating light 8.

Getting back to FIG. 5, it shows an operating light 8 in which a cover glass 82 protects the components placed to the frame part 81 of the operating light. Without deviating from the idea of the present invention, the operating light can also be implemented as a structure without the cover glass. It is essential that the projector 86 is integrated both structurally and operationally as a part of the operating light. That is, the control of the operation of the projector is a part of the operating light.

As well as, optionally, the control of operation of the stereo camera 87 arranged to the operating light and its signal routes can be arranged as a part of the operating light.

The cameras 87 are preferably arranged in the operating light 8 as directed to shoot primarily at the area whereto the operating light 8 is arranged to produce the above-discussed desired kind light pattern. On the other hand, the optics of the cameras can be arranged to enable an adjustment of their field of view (FOV). Also the direction the cameras shoot at can be arranged adjustable.

As the operating light according to the invention is already originally be designed to comprise a projector 87, and in various embodiments of the invention also two cameras, the design of the mechanism of its support structures is based on taking into account the extra mass added by those components which are additional to a traditional operating light.

Likewise, as far as there is a need to arrange additional cablings to the operating light for the projector, and optionally also the cameras, also the requirement of passing those through the support structures of the operating light can be taken into account when designing the operating light.

As to the camera units 805 they may include, as an example, a lens system and an image detector with their required and possible peripheral components. The operation of these components can relate to e.g. processing the detected image information or controlling of the lens system.

The lens system can comprise a lens with a fixed or adjustable focal length which lens forms an image on the detector. From the camera units 805, image information may be forwarded in digital form to the camera controller 806. It is possible to have the image information pre-processed in the camera units 805 before forwarding, e.g. by compensating defective pixels of the detector, by removing artefacts caused by the lens or by adjusting light exposure, sensitivity or color balance.

The camera controller 806 can include components the operation of which is related, in addition to the reception of signals and image information from the camera units 805 and, on the other hand, their forwarding, also to the processing and storing image information.

The camera controller 806, as well as the projector controller 802, may be arranged to receive information and signals from an external data system.

Thus, it is possible to perform the above-described image processings possibly implemented in the camera units 805 partially or totally just in the camera controller 806. The component utilized in the processing may be implemented as an ASIC- or FPGA-based solution, for instance. In forwarding data as well as in receiving data, it is possible to use e.g. WLAN or ETHERNET connections as an alternative for a cabling.

Figure 4:
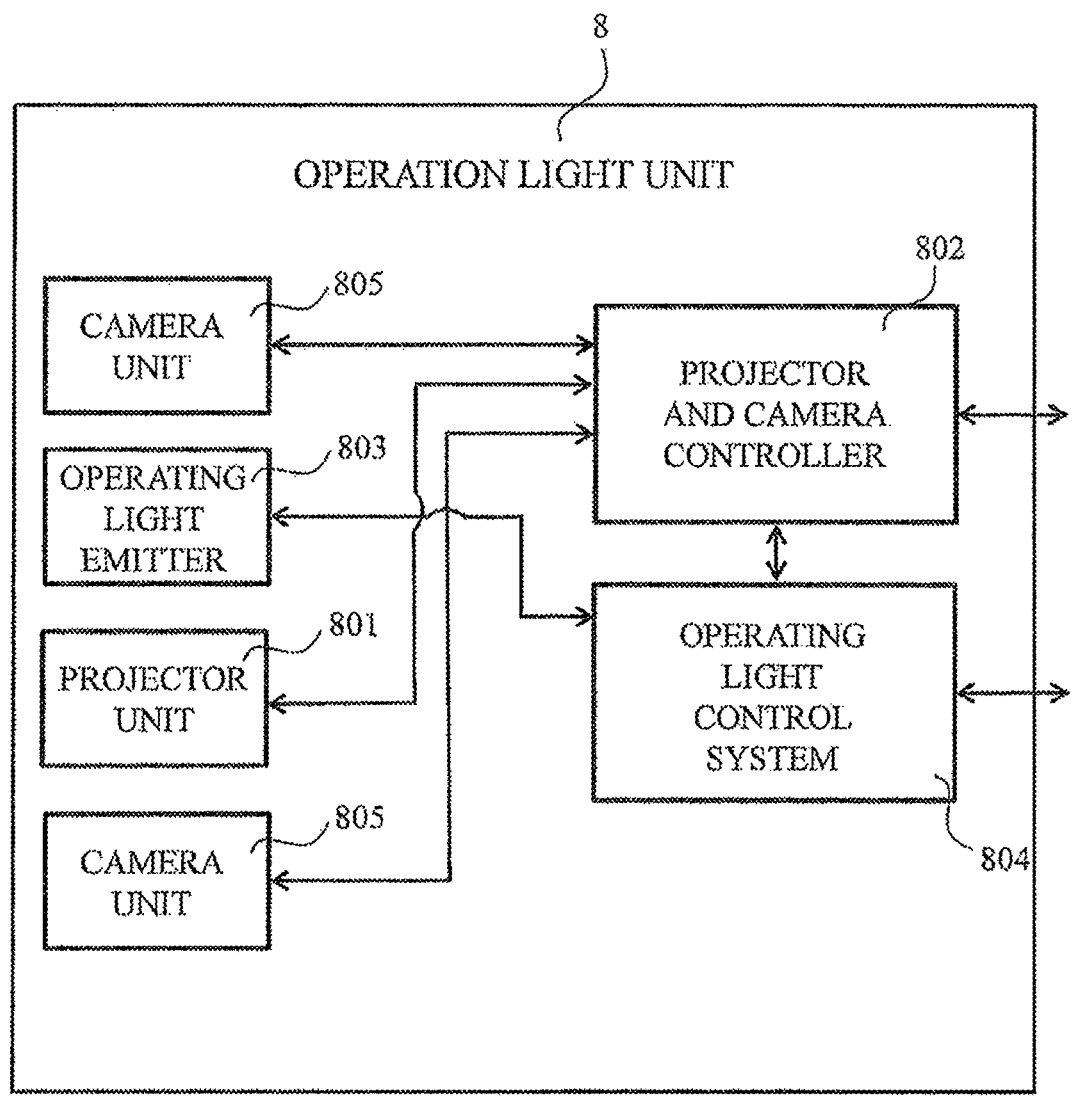
FIG. 4 shows a block diagram of another possible arrangement to implement the integration of the projector and the stereo camera to the dental operating light.

In the arrangements in accordance with FIGS. 2-4, the projector controller 802 is arranged into operational connection with the control system 804 of the operating light with which it can communicate and, particularly, from which it may be arranged to receive electricity. If required, it is possible to arrange to the projector controller 802 an arrangement which converts power being supplied to it into suitable voltages for the internal use of the projector controller 802 and also for the projector unit 801.

The same applies concerning the camera units 805 and the camera controller 806.

The control system 804 of the operating light can be in operational connection with the projector unit 801 and the light-emitter of the operating light 803. The light emitter 803 of the operating light 8 can comprise as the actual light-emitting component e.g. a LED arrangement and further optical components, such as one or more lenses and/or reflective surfaces.

In addition or instead, an operating light in general and applicable for use in the context of the invention may comprise more than one light sources and/or other kind of optics, such as one or more lenses and/or other kind reflective surfaces, for generating a desired kind light pattern in a desired direction and at a desired distance from the operating light. In general, the desired kind light pattern having desired properties substantially at a certain distance from the operating light, is generated by a dental operating light, which light pattern can then be positioned in the area of a patient's mouth such that the patient's oral cavity can be illuminated without the light glaring the patient.

As to the embodiment of the invention comprising the camera, the camera controller 806 may be arrange to receives from the camera units 805 image information in digital form and both the camera controller 806 and the camera unit 805 may be arranged to process information they receive. The camera controller 806 can also comprise a mass memory where image information detected and processed can be stored. Particularly, in embodiments where information is not forwarded from the operating light via a cable, it is preferable that image information can be compressed into an easily transferrable and storable format before forwarding.

The camera units 805 may be arranged to produce image information as a continuous stream of information which can be analyzed and processed within the camera system. Such processing can be based on control from outside the system or on analysis performed in the camera system itself. Information processing can be e.g. deleting information irrelevant with respect to its intended use before forwarding the information.

The analysis of image data can include e.g. identifying spatial frequency components and their intensity in different parts of the image, identifying patterns predefined to be detected as well as identifying their two-dimensional position, or calculating changes between successive images.

The processing of image information can again include e.g. processing the image into a form in which a part of the spatial frequency components of the image are presented by a smaller numeric accuracy than others, in which areas are deleted from the image information, or in which the image information is partially or totally replaced by results of an analysis.

In one embodiment, the above-mentioned stream of information refers to individual images ('frames') shot at high frequency. According to one preferred embodiment of the invention, the camera controller 806 is arranged to enable the control of such camera units 805 producing these individual images such that they can produce a pair of images shot substantially simultaneously. Then, it is possible to generate high-quality stereo images of the image information produced by the camera units 805.

In one embodiment, the control of operation of the cameras and the operating light is synchronized such that, to prevent overexposure of the images, the light is switched off for the time of shooting an image. It is thus possible to produce live image such that the operating light is flickered at a suitable frequency, which frequency is arranged to substantially correspond the image-shooting frequency.

In one preferred embodiment, the image detector and the optical components of the camera unit are located in the operating light structure such that their field of view opens from the same structure of the operating light, from the direction of the same surface from which also the light field of the operating light is emitted, and from inside the covers of the operating light.

It is possible to use the operating light including the camera construction for e.g. monitoring a dental care instrument, such as a drill. In such an arrangement, there is or there is added at a known point in the instrument a feature, a marker, which the cameras arranged in connection with the operating light image. A computer software in operational connection with the operating light is arranged to detect from the image information both the marker itself and its position and orientation in the image produced by the operating light.

Such detection function can be arranged to take place already in the operating light. The amount of information forwarded from the operating light can be decreased if, instead of the detected image information, only information on the position and orientation of the marker is forwarded.

To enable control of drilling, in addition to the detection of the position and orientation of the instrument, information is also required concerning how the marker arranged in connection with the instrument is positioned with respect to an anatomy being the target of the operation. This information can be obtained e.g. by arranging a different marker at a known point of the anatomy while it is also plausible to utilize as reference a surface model showing the intra-oral anatomy imaged by the cameras, which surface model is generated and can be updated from the image information produced by the camera pair arranged in the operating light.

If a method of the kind described above is applied to e.g. for drilling a hole in a jawbone for a dental implant, the information of the position and orientation of the instrument obtained in a way described above can be compared with a model of the anatomy being the target of the operation, to which model has also been modelled a hole designed for the implant. When all this information exists, there are various possible arrangements for its utilization. It is for example possible to visually indicate by using the projector arranged to the operating light the point where the instrument should be and, on the other hand, where it is at the present moment. This kind of system may be implemented to indicate when the instrument is at the point and orientation corresponding to the drilling plan, and/or when it is not. This information can be utilized even for controlling a robot performing the drilling.

As dental operating lights are also manufactured and sold as separate from an actual dental care unit, according to one aspect of the invention, one embodiment of the invention comprises a lighting system 83, 85 arranged to generate a desired kind light pattern in a desired direction and at a desired distance from the dental operating light, to illuminate a first area, and an articulated and balanced support arm structure 7 to support an operating light with such lighting system within an operating range of the arm structure 7, and further comprising a projector construction 86 configured to project graphics, pictures and/or video in essentially the same direction as the desired direction on a surface, the surface comprising a second area whereto the graphics, pictures and/or video is projected, the projector construction 86 being both structurally and operatively integrated into the dental operating light 8 to be a part of the dental operating light 8, and wherein the dental operating light 8 comprises, either, at least a mechanical connection construction or a signaling means compatible with corresponding means of a dental care unit.

Such operating light, even if not physically connected to a dental care unit, may comprise any feature of the invention as discussed above.

The invention claimed is:

1. A dental care unit construction, comprising:
a frame structure;
a first support construction for supporting at least one dental instrument used in connection with a dental care operation for treating a patient;
a control system;
a user interface;
an arrangement via which to said at least one instrument can be delivered power, or control signals, or both, needed for its operation, wherein to said at least one instrument is supplied power in the form of at least one of water and compressed air;
a dental operating light arranged for use in connection with dental care comprising a lighting system arranged to be able to generate a desired dental light pattern in a desired direction and at a desired distance from the operating light, to illuminate a first area, wherein the desired dental light pattern is a light pattern according to dental operating light standards according to which said light pattern is to be of a shape which illuminates a patient's oral cavity without glaring the patient's eyes;
a second support structure which supports the operating light, and—a projector construction configured to project graphics, pictures and/or video in essentially the same direction as said desired direction on a surface, the surface comprising a second area outside the first area whereto the graphics, pictures and/or video is projected, the projector construction being both structurally and operatively integrated into the operating light to be a part of the operating light of the dental care unit.

2. A dental care unit according to claim 1, wherein the projector construction is configured to project said graphics, pictures and/or video at said second area such that, at a proximity of said desired distance, said second area is outside but in close proximity to the first area.

3. A dental care unit according to claim 1, wherein said projector construction is configured to be controlled by a projector controller structurally integrated into the operating light.

4. A dental care unit according to claim 3, wherein said projector controller is configured to enable projecting said graphics, pictures and/or video, as a default or as a response to a control signal, at said second area, wherein at a proximity of said desired distance said second area is outside but in close proximity to the first area.

5. A dental care unit according to claim 3, wherein said projector controller is configured to project said graphics, pictures and/or video at a first part within said second area and simultaneously not to project anything on a second part within said second area.

6. A dental care unit according to claim 3, wherein said projector controller is configured to receive information relating to projecting said graphics, pictures and/or video from said dental instrument, which instrument may be one related to dental care or used in connection with a dental care operation, from a control system of either the instrument itself, or from the dental care unit when controlling operation of the dental instrument.

7. A dental care unit according to claim 1, wherein said projector construction is configured to project graphics, pictures and/or video such that said second area is larger than said first area.

8. A dental care unit according to claim 7, wherein said second area larger than the first area includes said first area.

9. A dental care unit according to claim 1, wherein said graphics, pictures and/or video comprises a user interface of the dental care unit or a part thereof.

10. A dental care unit according to claim 1, wherein the operating light is further arranged with at least one camera configured to shoot at least partly said second area.

11. The dental care unit of claim 10, wherein the light projector is configured to flicker at a suitable frequency arranged to substantially correspond to an image-shooting frequency of the camera.

12. A dental care unit according to claim 10, wherein the operating light comprises or is in functional connection with a means configured to recognize a gesture within a field of view of said at least one camera.

13. A dental care unit according to claim 12, wherein the control system of the dental care unit is configured to recognize a gesture shot by said at least one camera as a control signal when said gesture is made when said graphics, pictures and/or video is being projected by said projector and comprises a given feature of a user interface of the dental care unit.

14. A dental care unit according to claim 1, wherein a system including the dental care unit comprises a stereo camera arranged to the operating light, a means for pattern recognition and a means to project said graphics, pictures and/or video at an area covered by or comprising a given pattern configured to be recognized by said means for pattern recognition, and/or a means to project said graphics, pictures and/or video at an area outside the area covered by or comprising the given pattern configured to be recognized by said means for pattern recognition.

15. A dental care unit according to claim 1, wherein a system including the dental care unit comprises a stereo camera arranged to the operating light, a means for pattern recognition and a means to project at said second area a drilling plan including location and orientation of a hole to be drilled in an anatomy, together with an image or a part of an image shot by said stereo camera including a given pattern recognized by the means for pattern recognition, wherein said given pattern is a pattern arraigned to a dental drill instrument.

16. A dental care unit according to claim 1, wherein at least part of electronics of both the operating light itself and the projector, needed for their operation, is arranged as a physical part of a structure of the operating light.

17. A dental care unit according to claim 1, wherein the desired light pattern satisfies ISO 9680-Dentistry-Operating Lights.

18. The dental care unit of claim 1, wherein the second area comprises patient eye protectors or an added reflector surface.

19. The dental care unit of claim 1, wherein the operating light and projector construction share a common cover.

* * * * *